US008684233B2

(12) United States Patent
Nishio et al.

(10) Patent No.: US 8,684,233 B2
(45) Date of Patent: Apr. 1, 2014

(54) FLUID CONTAINER UNIT AND METHOD FOR INJECTING DIFFERENT KINDS OF FLUIDS INTO FLUID USAGE EQUIPMENT

(75) Inventors: Suguru Nishio, Osaka (JP); Kojiro Kotani, Tokyo (JP); Ryo Inoue, Tokyo (JP); Takayoshi Iwanami, Tokyo (JP); Yoshiyuki Sato, Tokyo (JP)

(73) Assignees: Saraya Co., Ltd., Osaka (JP); Olympus Medical Systems Corp., Tokyo (JP)

( * ) Notice: Subject to any disclaimer, the term of this patent is extended or adjusted under 35 U.S.C. 154(b) by 102 days.

(21) Appl. No.: 13/124,165

(22) PCT Filed: Oct. 15, 2009

(86) PCT No.: PCT/JP2009/067850
§ 371 (c)(1),
(2), (4) Date: Jul. 7, 2011

(87) PCT Pub. No.: WO2010/044442
PCT Pub. Date: Apr. 22, 2010

(65) Prior Publication Data
US 2011/0253739 A1    Oct. 20, 2011

(30) Foreign Application Priority Data
Oct. 17, 2008 (JP) ................................. 2008-268491

(51) Int. Cl.
*B67D 7/78*    (2010.01)
(52) U.S. Cl.
USPC ............... 222/145.1; 222/1; 222/81; 222/86; 222/87; 222/129; 222/145.5; 222/153.01
(58) Field of Classification Search
USPC ...................... 222/1, 80–81, 86–88, 94, 129, 222/136–137, 145.5, 325, 145.6, 562, 222/153.01, 153.13, 145.1
See application file for complete search history.

(56) References Cited

U.S. PATENT DOCUMENTS 3,767,085 A * 10/1973 Cannon et al. .................. 222/82
4,771,919 A *  9/1988 Ernst .............................. 222/134
(Continued)

FOREIGN PATENT DOCUMENTS

CN    101011235    8/2007
JP    4-50684    4/1992
(Continued)

OTHER PUBLICATIONS

Extended European Search Report (in English language) issued Mar. 5, 2012 in corresponding European Patent Application No. 09 82 0620.

(Continued)

*Primary Examiner* — Frederick C Nicolas
(74) *Attorney, Agent, or Firm* — Wenderoth, Lind & Ponack, LLP

(57) ABSTRACT

A fluid container unit including: a container coupling for coupling a supply/discharge port of a first container with a supply/discharge port of a second container; a single nozzle member having a nozzle tube; a connection cap having a first end for holding a base portion of the nozzle member and a second end for covering one side of the container coupling by fitting around an outer periphery thereof; an intermediate adaptor having a pair of pusher elements facing the first and the second supply/discharge ports, respectively; and a supply/discharge port opening mechanism for moving the intermediate adaptor toward the container coupling and opening the supply/discharge ports by the pusher elements. The pusher elements are movably held in a direction along a longitudinal axis of the nozzle tube in the connection cap.

14 Claims, 11 Drawing Sheets

(56) References Cited

U.S. PATENT DOCUMENTS

| | | | | |
|---|---|---|---|---|
| 4,838,457 | A | * | 6/1989 | Swahl et al. .................... 222/48 |
| 4,871,090 | A | * | 10/1989 | Hoffmann ....................... 222/81 |
| 4,989,758 | A | * | 2/1991 | Keller ........................... 222/137 |
| 5,152,432 | A | * | 10/1992 | De Laforcade ............. 222/145.1 |
| 5,526,957 | A | * | 6/1996 | Brown et al. ................... 222/94 |
| 5,566,860 | A | * | 10/1996 | Schiltz et al. .................. 222/94 |
| 5,875,928 | A | * | 3/1999 | Muller et al. ................... 222/82 |
| 6,341,716 | B1 | * | 1/2002 | Goettner et al. ................ 222/94 |
| 6,352,177 | B1 | * | 3/2002 | Bublewitz et al. .............. 222/82 |
| 6,398,077 | B1 | * | 6/2002 | Gross et al. ................ 222/145.1 |
| 6,834,778 | B2 | * | 12/2004 | Jinbo et al. .................... 222/135 |
| 6,837,612 | B2 | * | 1/2005 | Bublewitz et al. ......... 366/172.1 |

| | | |
|---|---|---|
| 2007/0193605 | A1 | 8/2007 Kuroshima et al. |

FOREIGN PATENT DOCUMENTS

| | | |
|---|---|---|
| JP | 2004-182258 | 7/2004 |
| JP | 2004-331101 | 11/2004 |
| JP | 2006-43190 | 2/2006 |
| JP | 2007-202859 | 8/2007 |
| JP | 2008-133045 | 6/2008 |

OTHER PUBLICATIONS

International Search Report issued Jan. 19, 2010 in International (PCT) Application No. PCT/JP2009/067850.

* cited by examiner

FLUID CONTAINER UNIT AND METHOD FOR INJECTING DIFFERENT KINDS OF FLUIDS INTO FLUID USAGE EQUIPMENT

BACKGROUND OF THE INVENTION

1. Technical Field

The present invention relates to a fluid container unit configured by integrally-assembling two containers for respectively accumulating different kinds of fluids.

2. Description of the Related Art

Conventionally, in cleaning or sterilizing items such as relatively small medical instruments, a method for applying a predetermined drug solution (cleaning solution or sterilizing solution) onto the surfaces of the instruments in a constant-volume tank (cleaning/sterilizing tank) has been widely employed. In this method, the instrument is pretreated by a preliminary cleaning, and is placed in the cleaning/sterilizing tank. Then a cleaning or sterilizing treatment is conducted in the cleaning/sterilizing tank by applying a drug solution onto the surface of the instrument by spraying, dipping and the like. For example, Japanese Patent Laid-Open Publication No. 2006-43190 discloses an endoscope cleaning/sterilizing apparatus for conducting cleaning/sterilizing treatment of the endoscope by using the above-mentioned method.

As a drug solution which is used for such a sterilizing treatment, there is known a type of drug solution which is capable of achieving a higher sterilizing effect by mixing two kinds of drug solutions, and thereafter applying the mixed solution onto the surface of the objective article. In using this type of drug solution, it is common to prepare two bottles respectively containing a drug solution which is to be mixed with each other, and sequentially fixing those two bottles to the injection site of the fluid usage equipment (for example, a cleaning/sterilizing apparatus for endoscopic instruments), and thereafter sequentially supplying those two kinds of drug solutions into the tank.

SUMMARY OF THE INVENTION

1. Problems to be Solved by the Invention

However, in the method of preparing two bottles respectively containing two types of drug solutions, and sequentially fixing those two bottles to the injection site of the drug solution tanks, the task of supplying the drug solutions to the drug solution tanks is very cumbersome and troublesome, and furthermore, there is a possibility of taking and using the wrong bottle by error.

Thus, consideration is made in unitizing the two bottles respectively containing different drug solutions into one set and integrally handling the same. In such a case, it is convenient to unitize the two bottles in a parallel arrangement such that the respective bottle center lines are parallel. With such unitization, the two types of bottles can be fixed to the injection site of the drug solution tank without being mistaken, and the two types of drug solutions can be simultaneously injected into the tank.

However, when the two bottles are simply unitized in parallel arrangement, two injection ports must be provided on the injection side of the unit. Therefore, in this case, the injection site of the drug solution tank of the fluid usage equipment also needs to be able to receive two injection ports, which becomes one inhibiting factor in making the fluid usage equipment compact. Moreover, the two injection ports must be accurately aligned and fixed to the receiving ports of the injection site when fixing the injection ports of the unit to the injection site of the drug solution tank of the fluid usage equipment, which is a drawback in enhancing the fixing workability.

It is a basic object of the present invention to provide a fluid container unit in which the fixing workability to the injection site of the fluid usage equipment is more satisfactory and the injection site is made more compact when unitizing two containers respectively storing different types of fluid so that it can be integrally handled.

2. Means for Solving the Problems

In order to achieve the objects, the present invention provides a fluid container unit configured by integrally-assembling a first container and a second container for respectively accumulating different kinds of fluids in a parallel arrangement. The fluid container unit includes: a container coupling for coupling a first supply/discharge port located at one end of the first container with a second supply/discharge port located at one end of the second container; a single nozzle member having a nozzle tube; a connection cap having one end for holding a base portion of the nozzle member and another end for covering one side of the container coupling by fitting around an outer periphery thereof; an intermediate adaptor having a pair of pusher elements facing the first and the second supply/discharge ports respectively, and being held movably in a direction along a longitudinal axis of the nozzle tube in the connection cap; and a supply/discharge port opening mechanism for moving the intermediate adaptor toward the container coupling and opening the first and the second supply/discharge ports by the pair of pusher elements.

In this construction, the first container and the second container are securely integrated with the container coupling for coupling the first supply/discharge port and the second supply/discharge port. As the intermediate adaptor moves toward the container coupling along the longitudinal axis of the nozzle tube in the connection cap, the first and the second supply/discharge ports are opened by the pair of pusher elements arranged in the intermediate adaptor, and the fluids inside the first and the second containers are simultaneously discharged and injected at the injection site of the fluid usage equipment in a mixed state. Furthermore, since a single nozzle is arranged on one end side (injection side) of the fluid container unit, the fixing workability of the fluid container unit becomes more satisfactory and the injection site of the fluid usage equipment can be made more compact compared to the case where two injection ports must be handled.

In the above case, preferably, the base portion of the nozzle member is held rotatably around the longitudinal axis of the nozzle tube at one end of the connection cap; and the nozzle member is configured so as to be removably fixed to an injection site of a fluid usage equipment. Further, the supply/discharge port opening mechanism includes a first inclined surface part which is provided on an inner surface of the nozzle member and is inclined along a rotational direction of the nozzle member, and a second inclined surface part which is provided on an outer surface of the intermediate adaptor and is to be associated with the first inclined surface part. Rotating the nozzle member by a required angle in one direction causes the first inclined surface part to rotate by a required angle in one direction and the second inclined surface part to be pushed toward the opposite-nozzle member side, thereby the intermediate adaptor is moved toward the container coupling by a predetermined amount, and the pair of pusher elements open the first and the second supply/discharge ports.

In this construction, the base portion of the nozzle member is held rotatably around the longitudinal axis of the nozzle tube at one end of the connection cap, the nozzle tube is configured so as to be removably fixed to an injection site of a fluid usage equipment, and the intermediate adaptor is reliably moved toward the container coupling by a predetermined amount so that the pair of pusher elements open the first and the second supply/discharge ports, through the first and the second inclined surface parts, by merely rotating the nozzle member by a required angle in one direction.

Further, in this case, more preferably, by inserting the nozzle tube of the nozzle member into the injection site of the fluid usage equipment, and thereafter rotating the nozzle member by the required angle in the one direction while maintaining the insertion state, the nozzle tube is removably fixed to the injection site of the fluid usage equipment, and the intermediate adaptor is moved toward the container coupling by the predetermined amount, and the pair of pusher elements open the first supply/discharge port and the second supply/discharge port.

In this construction, by inserting the nozzle tube into the injection site of the fluid usage equipment, and thereafter, rotating the nozzle member with respect to the connection cap while maintaining the insertion state, the nozzle tube can be removably fixed to the injection site of the fluid usage equipment in a one touch operation, and the first and the second supply/discharge ports are opened by the pair of pusher elements arranged in the intermediate adaptor, so that the fluids in the first and the second containers are simultaneously discharged and injected at the injection site of the fluid usage equipment in the mixed state.

In the above-mentioned cases, more preferably, the fluid container unit further includes an adaptor holding mechanism which holds the intermediate adaptor in a position where the pair of pusher elements are kept away from the first and the second supply/discharge ports, in an unfixed state in which the nozzle tube is not fixed to the injection site of the fluid usage equipment.

In this construction, the pair of pusher elements are reliably prevented from opening the first and the second supply/discharge ports in the unfixed state.

In this case, more preferably, the adaptor holding mechanism includes an adaptor retaining portion provided on an inner surface of the nozzle member, and a retained portion which is provided on an outer surface of the intermediate adaptor and associated with the adaptor retaining portion. The intermediate adaptor is held in a position where the pusher elements are kept away from the first and the second supply/discharge ports, in an adaptor retained state where the retained portion of the intermediate adaptor is retained by the adaptor retaining portion of the nozzle member. Also, by rotating the nozzle member in one direction from the adaptor retained state, the adaptor retaining portion is rotated in the one direction and released from the retained portion, thereby the adaptor retained state is released and the intermediate adaptor holding state is released, and further thereby the intermediate adaptor is allowed to move toward the container coupling.

In this construction, the pair of pusher elements are reliably maintained in a state where they are kept away from the first and the second supply/discharge ports by maintaining the adaptor retained state, and the intermediate adaptor including the pair of pusher elements is reliably allowed to move toward the container coupling by simply rotating the nozzle member in one direction from the adaptor retained state.

More preferably, the base portion of the nozzle member is held by fitting at the one end of the connection cap; at a fitting portion between the base portion of the nozzle member and the connection cap, a click sense providing mechanism for providing a click sense to a rotating operation of the nozzle member in accordance with a required rotation angle of the nozzle member which is enough to let the intermediate adaptor move toward the container coupling by the predetermined amount; and the required rotation angle of the nozzle member is set to be larger by a predetermined angle than a rotation angle that is sufficient to put the nozzle tube into a fixed state at the injection site of the fluid usage equipment.

In this construction, when the intermediate adaptor moves toward the container coupling by a predetermined amount and the pair of pusher elements open the first and the second supply/discharge ports in the rotating operation of the nozzle member, this is detected by the click sense at the time of the rotating operation. The nozzle tube is reliably fixed to the injection site of the fluid usage equipment at the point in time when the click sense is detected.

In the above-mentioned cases, more preferably, first and second closing seal pieces are attached at the first and second supply/discharge ports, respectively, for closing the first and second supply/discharge ports in an unfixed state in which the nozzle tube is not fixed to the injection site of the fluid usage equipment. The pair of pusher elements open the first and second supply/discharge ports by pushing open the first and the second closing seal pieces, respectively; and each of the supply/discharge ports is separated into two apertures by a push-opened closing seal piece. Also, the fluid in the container is supplied to the nozzle member side through one aperture, while air is introduced into the container through the other aperture.

In this construction, the closing seal piece, which is push-opened by the pusher element, separates the supply/discharge port into two apertures, and the fluid in the container is supplied toward the nozzle member from one aperture while air is introduced into the container from the other aperture, so that the air is easily introduced into the container and smooth fluid supply with suppressed pulsation can be carried out.

Further, in the above-mentioned cases, more preferably, the first and the second containers respectively are provided with first and second supply/discharge cylinders respectively projecting from one end of the containers. The first and the second supply/discharge ports are formed inside the supply/discharge cylinders; and the container coupling is provided with a coupling wall for coupling the first supply/discharge cylinder and the second supply/discharge cylinder, an outer peripheral wall surrounding the coupling wall at a predetermined distance therefrom and a flat portion for connecting another end of the outer peripheral wall and another end of the coupling wall. Also, the intermediate adaptor is provided with an adaptor wall for surrounding the pair of pusher elements. Also, an end surface of the adaptor wall abuts against the flat portion of the container coupling, in a state in which the pair of pusher elements open the first and the second supply/discharge ports by moving the intermediate adaptor toward the container coupling side.

In this construction, the end face of the adaptor wall is abutted against the flat portion of the container coupling in a state where the first and the second supply/discharge ports are opened by the pair of pusher elements, thereby the fluid discharged from the first and the second supply/discharge ports is suppressed from leaking out to the exterior of the adaptor wall.

In this case, more preferably, at least one of the coupling wall, the outer peripheral wall and the adaptor wall are provided with an adaptor wall hold mechanism for keeping the end surface of the adaptor wall in an abutting state against the flat portion of the container coupling, by locking the adaptor wall with at least one of the coupling wall and the outer peripheral wall.

In this construction, the end face of the adaptor wall is held more reliably and stably in the abutted state against the flat portion of the container coupling.

Still further, in the above-mentioned cases, more preferably, another side of the connection cap is provided with a container side wall locking part for locking each side wall of the first and the second containers, and each side wall of the first and the second containers is provided with a locked portion for being locked by the container side wall locking part.

In this construction, not only the first and the second supply/discharge ports at one end of the first and the second containers are coupled by the container coupling, but also the side wall of each container is locked to the other side of the connection cap, and thereby the first container and the second container are more securely integrated, and, for example, twist deformation and the like of the entire unit can also be effectively suppressed.

3. Effects of the Invention

According to the present invention, in a fluid container unit configured by integrally assembling a first container and a second container, which respectively store different types of fluids, in a parallel arrangement, the first container and the second container can be securely integrated and assembled by coupling, with a container coupling, a first supply/discharge port positioned on one end side of the first container and a second supply/discharge port positioned on one end side of the second container. Furthermore, with the arrangement of the supply/discharge port opening mechanism, the intermediate adaptor can be moved toward the container coupling along the longitudinal axis of the nozzle tube in the connection cap to open the first and the second supply/discharge ports by the pair of pusher elements arranged in the intermediate adaptor to simultaneously discharge the fluids in the first and the second containers and to inject them to the injection site of the fluid usage equipment. Moreover, merely a single nozzle is arranged on one end side (injection side) of the fluid container unit, and the fluids in the first and the second containers are injected at the injection site of the fluid usage equipment through the single nozzle, and hence, the fixing work to the injection site of the fluid usage equipment can be more easily and rapidly carried out and the workability thereof is greatly enhanced in comparison with the case where two injection ports are lined. The fluids in the first and second containers that are simultaneously discharged from the first and the second supply/discharge ports are mixed in the process of being sent through the single nozzle member, and are injected at the injection site of the fluid usage equipment in a mixed state, whereby a more satisfactory mixed state can be obtained. The injection site of the fluid usage equipment merely needs to receive the single nozzle since only a single nozzle is arranged on the injection side of the fluid container unit, and hence the injection site of the fluid usage equipment can be made more compact compared to the case of receiving two injection ports.

DESCRIPTION OF THE REFERENCE NUMERALS

Figure 1:
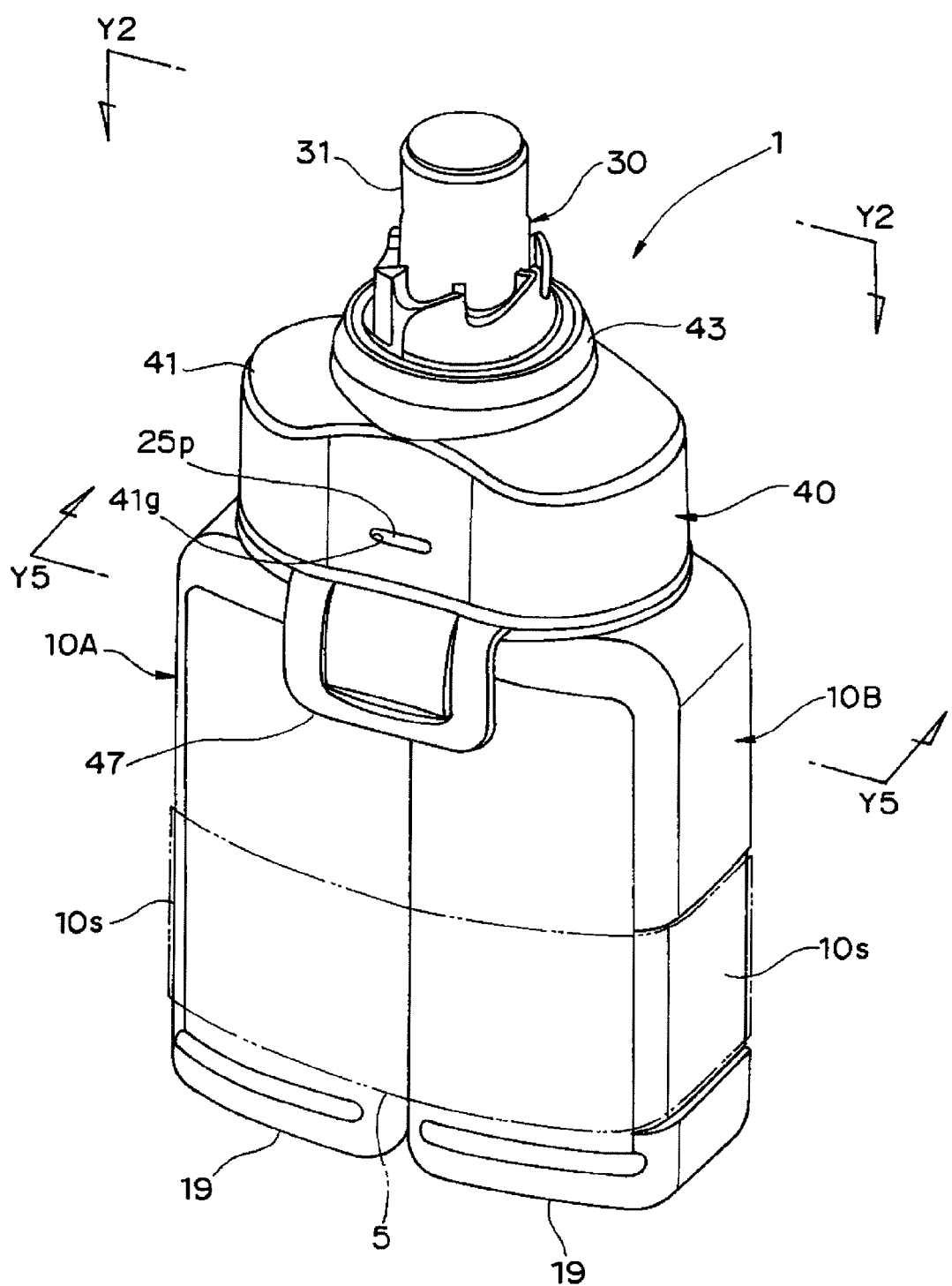
FIG. 1 is an overall perspective view illustrating a fluid container unit constructed in accordance with an embodiment of the present invention in an unused state.

1 Fluid container unit
10A First container
10B Second container
10g Fitting groove
11 Supply/discharge cylinder
16 Supply/discharge port
16a Inside aperture
16b Outside aperture
18 Closing seal piece
20 Container coupling
21 Coupling wall
25 Outer peripheral wall
25p Locking portion
27 Flat portion
30 Nozzle member
30d Adapter retaining detent
30f First inclined surface part
31 Nozzle tube
34 Base portion of the nozzle member
34p Small projection
40 Connection cap
43 Nozzle holder portion
43c Engagement recess
47 Container side wall locking part
48 Locking rib
50 Intermediate adaptor
50f Second inclined surface part
50g Retained groove
51 Adaptor tube
56 Adaptor wall
58 Pusher element

DETAILED DESCRIPTION OF THE INVENTION

Hereinafter, an embodiment of the present invention will be explained in detail with reference to the accompanying drawings.

Figure 2:
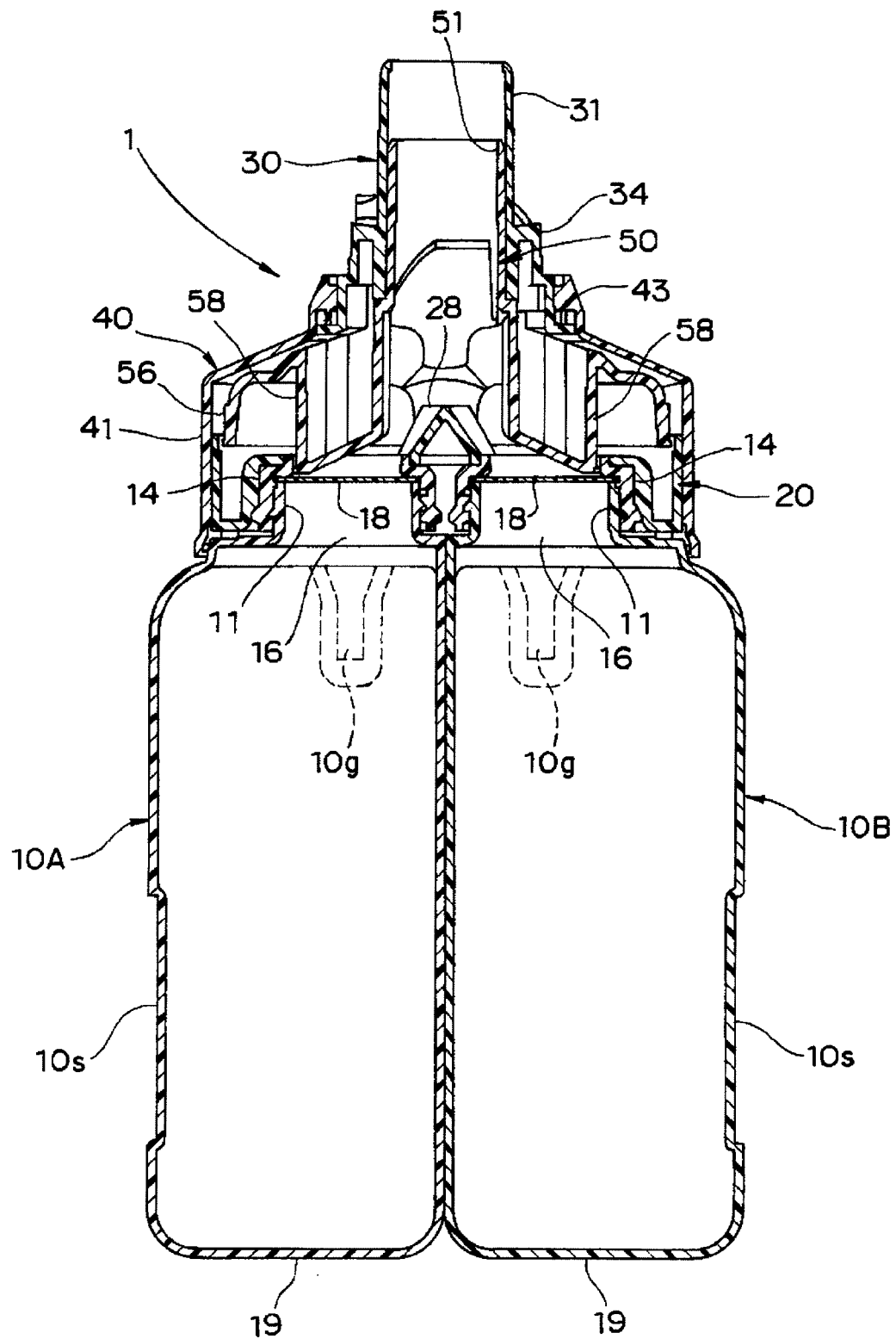
FIG. 2 is an overall vertical cross-sectional view of the fluid container unit taken along a line Y2-Y2 in FIG. 1.
Figure 3:
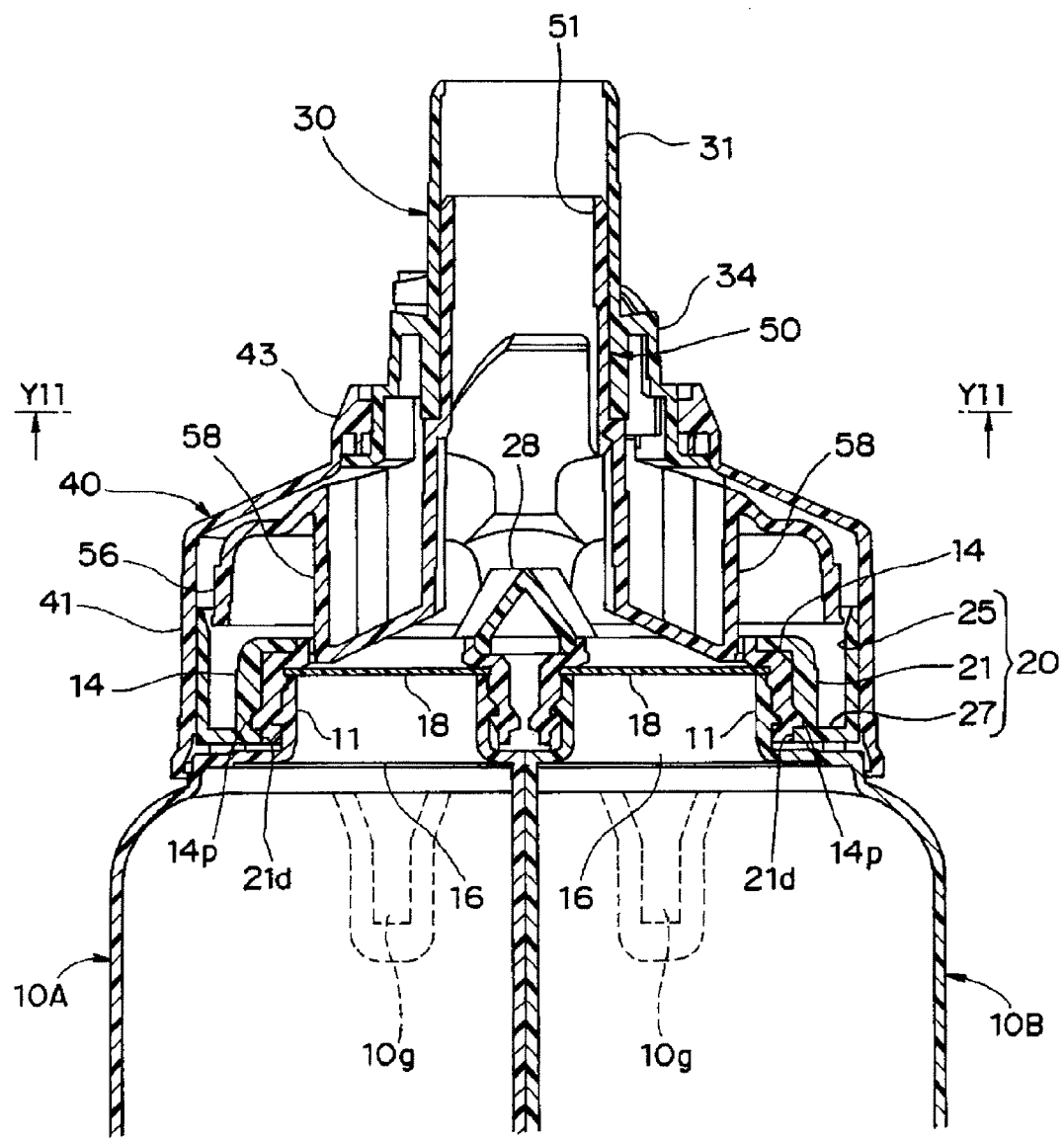
FIG. 3 is an enlarged vertical cross-sectional view of a critical portion of the fluid container unit illustrating an enlarged critical portion of FIG. 2.
Figure 4:
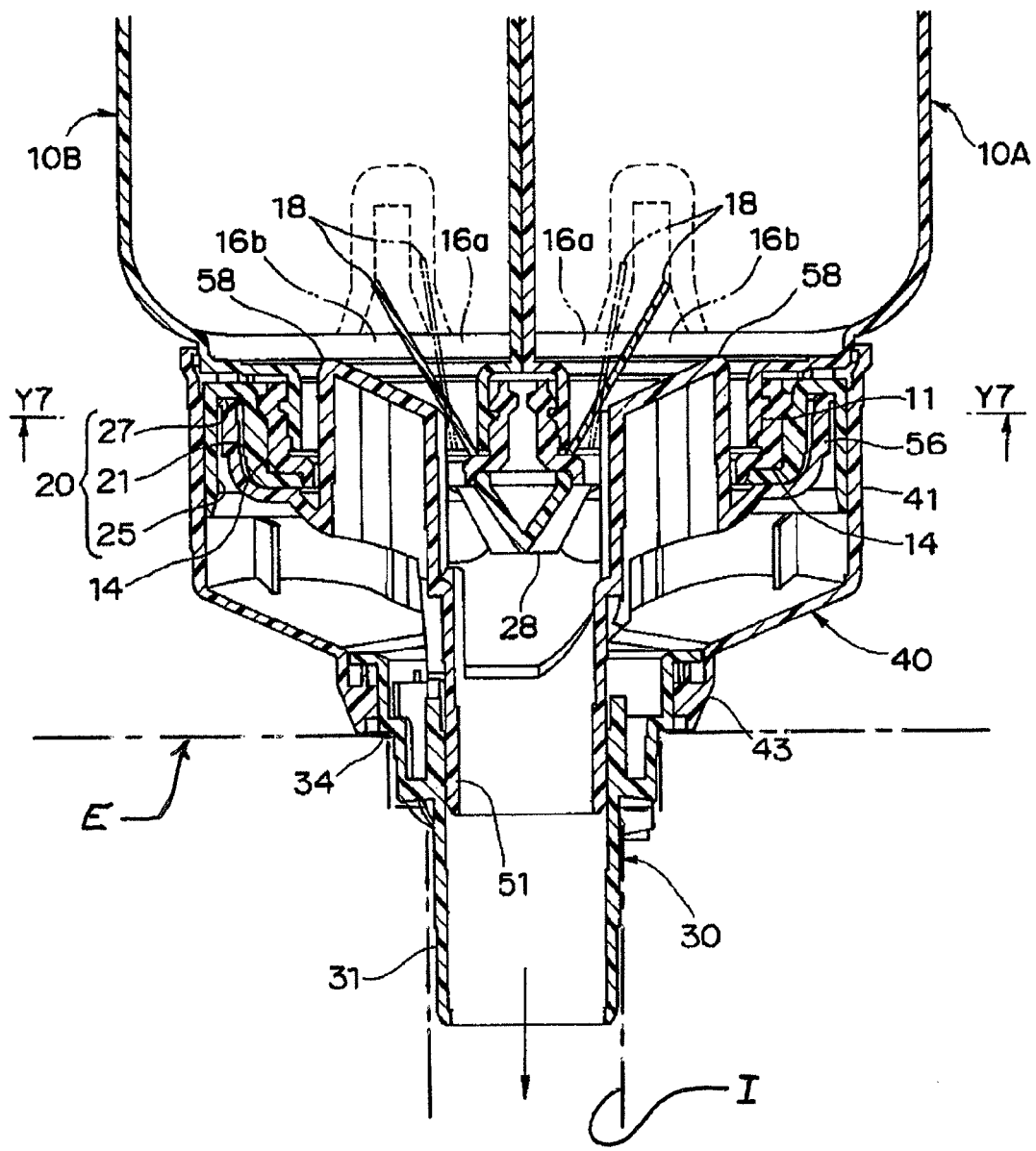
FIG. 4 is an enlarged vertical cross-sectional view of a critical portion of the fluid container unit corresponding to FIG. 3, which shows the fluid container unit in a usage state.
Figure 5:
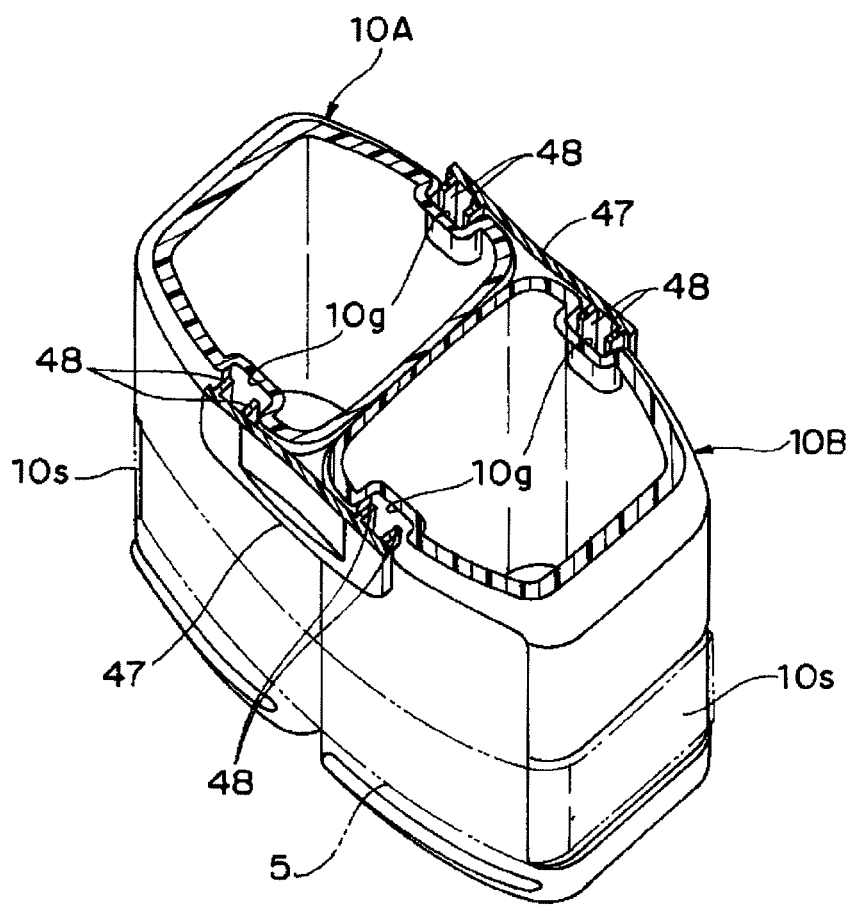
FIG. 5 is a perspective view showing a horizontal cross-section of the fluid container unit taken along a line Y5-Y5 in FIG. 1.

FIG. 1 is an overall perspective view illustrating a whole construction of a fluid container unit in accordance with the present embodiment in an unused state, FIG. 2 is an overall vertical cross-sectional view of the fluid container unit taken along a line Y2-Y2 in FIG. 1, FIG. 3 is an enlarged vertical cross-sectional view of a critical portion of the fluid container unit illustrating an enlarged critical portion of FIG. 2, and FIG. 4 is an enlarged vertical cross-sectional view of a critical portion of the fluid container unit corresponding to FIG. 3, which shows the fluid container unit in a usage state. FIG. 5 is a perspective view showing a horizontal cross-section of the fluid container unit taken along a line Y5-Y5 in FIG. 1.

The fluid container unit 1 in accordance with the present embodiment is normally placed with a bottom surface 19 of each container 10A, 10B facing to the lower side and a distal end of a nozzle 31 facing to the upper side when not in use such as in a time of storage or in a time of transportation (see FIG. 1 and FIG. 2). When fixing to the injection site I of the fluid usage equipment E (e.g., cleaning agent tank of an apparatus for cleaning an endoscope) in time of use, the fluid container unit 1 is turned upside down (see FIG. 4) so that the distal end of the nozzle 31 is facing to the lower side or the distal end of the nozzle 31 is facing diagonally to the lower side according to the direction of the injection site I.

Since the up and down directivity of the fluid container unit 1 normally differs when not in use and when in use, the upper side when not in use (upper side in FIG. 1 and FIG. 2; distal end side of nozzle 31) is referred to as "one side" and the lower side when not in use (lower side in FIG. 1 and FIG. 2; bottom surface 19 side of container) is referred to as the "other side" in the following description. Therefore, the "one side" of the fluid container unit 1 corresponds to the fluid discharging side when using the container.

As is apparent from FIG. 1 and FIG. 2, the fluid container unit 1 is configured by integrally assembling and unitizing a first container 10A and a second container 10B, which respectively contain different types of fluids. The integral assembly is a parallel arrangement such that the center lines in the longitudinal direction (up and down direction in FIG. 1 and FIG. 2) of each container 10A, 10B become substantially parallel.

The fluid container unit 1 is used, for example, to supply a predetermined sterilizing agent to a sterilizing agent tank of an apparatus for cleaning the endoscope (both are not illustrated), where the first container 10A and the second container 10B respectively store a first agent and a second agent of a liquid sterilizing agent used for the sterilizing treatment of the endoscope. The first agent and the second agent express high sterilizing/bactericidal power by being mixed, and are used in a sufficiently mixed state.

When using the two types of different fluids (first agent, second agent) by mixing, the two kinds of fluid containers can be fixed to the injection site of the fluid usage equipment (sterilizing agent tank of the apparatus for cleaning the endoscope) without being mistaken, and the two types of fluid can be simultaneously injected into the equipment by integrally assembling and unitizing the two containers (first container 10A, second container 10B), which respectively contain the two fluids. Therefore, improper usage due to mix up of the fluid containers, and the like can be reliably prevented, and the task of injecting the fluids at the injection site of the fluid usage equipment can be simplified compared to the case in which the fluid containers 10A, 10B are individually handled.

As shown in detail in FIG. 2 to FIG. 4, the fluid container unit 1 includes, in addition to the first container 10A and the second container 10B, a container coupling 20 for coupling both of the containers, a single nozzle member 30, a connection cap 40 for covering one side (upper side in FIG. 1 to FIG. 4) of the container coupling 20, an intermediate adaptor 50 held in the connection cap 40, and the like, as major constituent elements. These constituent elements will be described below.

As is apparent from FIG. 1 and FIG. 2, the first container 10A and the second container 10B are formed in a hollow substantially rectangular parallelepiped shape, where one end side (upper end side in FIG. 1 and FIG. 2) includes a first supply/discharge port 16 and a second supply/discharge port 16 having a circular shape (see FIG. 2 to FIG. 4), respectively. The supply/discharge ports 16, 16 are respectively formed by a first supply/discharge cylinder 11 and a second supply/discharge cylinder 11 having a cylindrical shape arranged to respectively project out from the one end of each container 10A, 10B. As more specifically shown in FIG. 3 and FIG. 4, a male screw (thread) is screw-formed on the outer periphery of each supply/discharge cylinder 11, 11, and a cap 14 (supply/discharge cylinder cap) is screw-fitted and tightened to the male screw. A circular plate shaped closing seal piece 18 having a predetermined thickness for closing and sealing each supply/discharge port 16 is attached and fixed between the back surface side of the distal end portion (upper end portion in FIG. 2) of the supply/discharge cylinder cap 14 and the distal end face of the supply/discharge cylinder 11.

The first container 10A and the second container 10B are preferably obtained by molding synthetic resin material into a hollow substantially rectangular parallelepiped shape using a predetermined molding die. The supply/discharge cylinder cap 14 and the closing seal piece 18 are also preferably made of synthetic resin.

In the present embodiment, the supply/discharge port 16 and the supply/discharge cylinder 11 are arranged at positions that deviate in a predetermined direction from the center line in the longitudinal direction of each container 10A, 10B. The containers 10A, 10B are integrally assembled in parallel arrangement with predetermined side surfaces abutting each other such that the respective supply/discharge ports 16 and the supply/discharge cylinders 11 are brought close to each other.

The container coupling 20 couples the first supply/discharge port 16 and the second supply/discharge port 16 respectively positioned on the one end sides of the first container 10A and the second container 10B, and includes a coupling wall 21 for coupling the first supply/discharge cylinder 11 and the second supply/discharge cylinder 11 (more specifically, coupling the supply/discharge cylinder caps 14 which are tightened and fixed to the outer periphery of the respective supply/discharge cylinders 11), an outer peripheral wall 25 for surrounding the coupling wall 21 with a predetermined spacing, and a flat portion 27 for connecting an end (lower end in FIG. 3) of the outer peripheral wall 25 and an end of the coupling wall 21, as specifically shown in FIG. 3.

Figure 6:
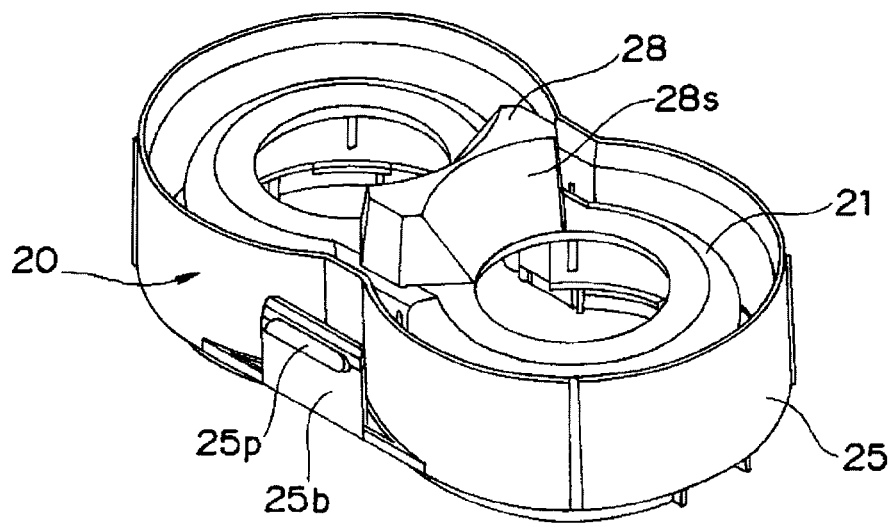
FIG. 6 is an overall perspective view of a container coupling.

FIG. 6 is an overall perspective view of the container coupling 20, where a central guide 28, including a pair of inclined guide surfaces 28s that connect to one end of each supply/discharge cylinder cap 14. The guide surfaces are formed such that one end side is pointed and is arranged at the middle on one end side of the coupling wall 21, as is apparent from the figure. The central guide 28 has a guiding action for discharging the fluid from each supply/discharge port 16 to one side as smooth as possible.

Figure 7:
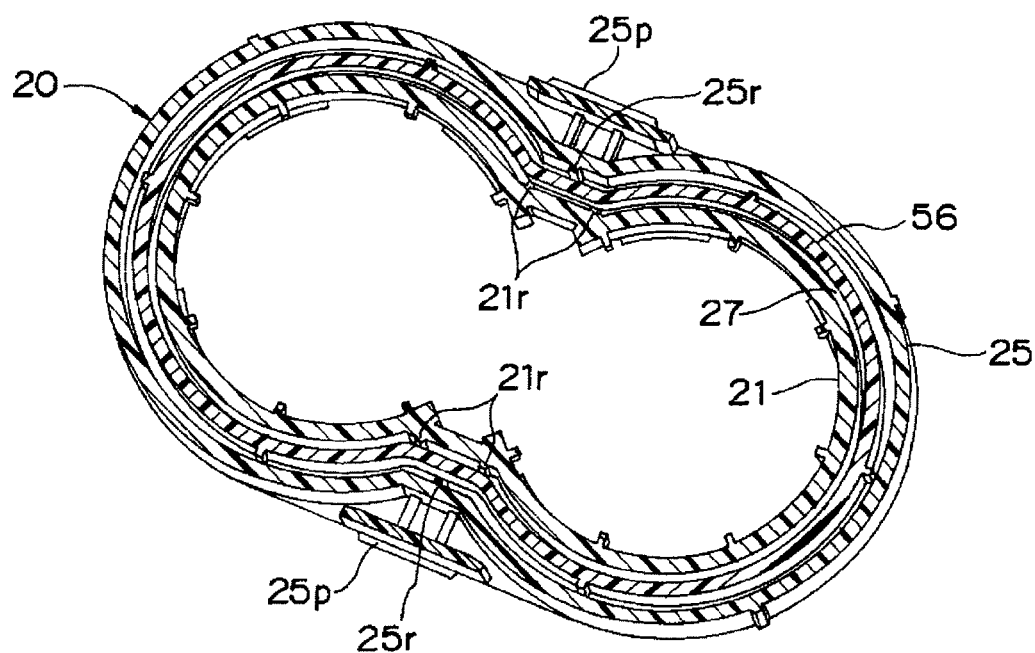
FIG. 7 is an illustrative drawing which shows a critical portion of a cross-sectional view of the container coupling and an adaptor wall taken along a line Y7-Y7 in FIG. 4.
Figure 8:
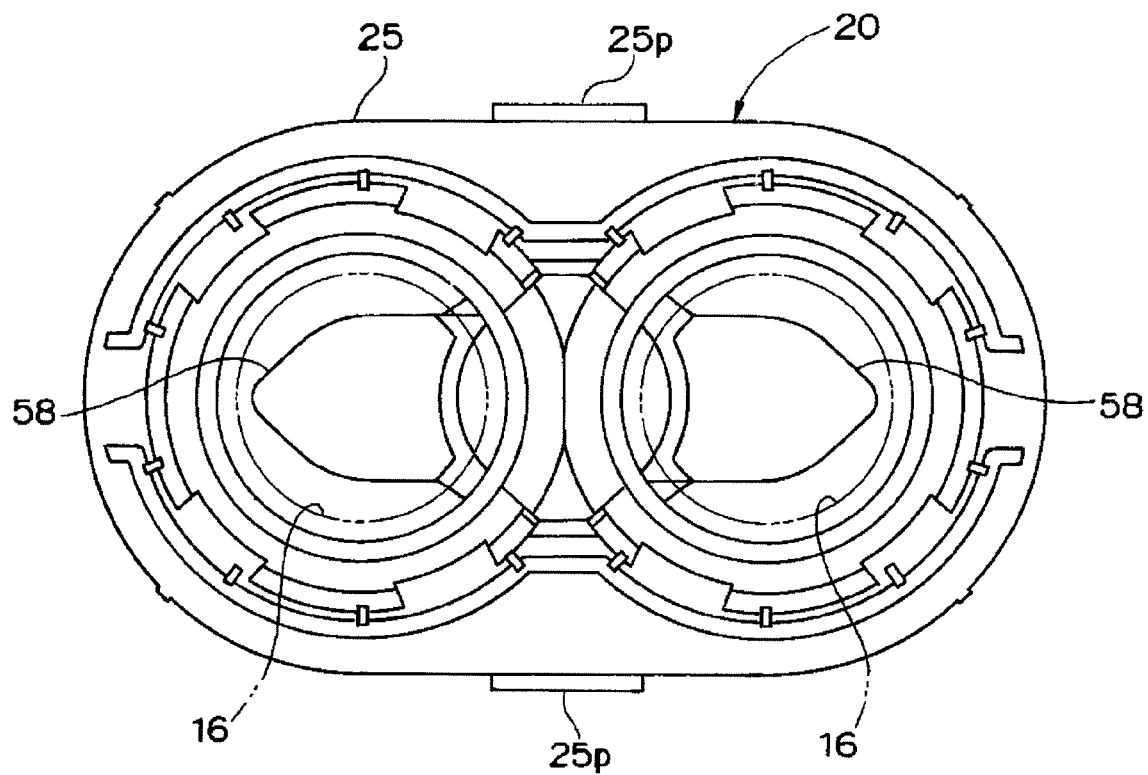
FIG. 8 is an illustrative drawing showing an assembled state of the container coupling and an intermediate adaptor.

FIG. 7 shows a critical portion of a cross-sectional view of the container coupling 20 and an adaptor wall 56 of an intermediate adaptor 50 taken along a line Y7-Y7 in FIG. 4, and shows a state in which the adaptor wall 56 of the intermediate adaptor 50, to be described later, is positioned between the coupling wall 21 and the outer peripheral wall 25 of the container coupling 20 in the usage state of the container unit 1. FIG. 8 is an illustrative drawing which shows an assembled state of the container coupling 20 and the intermediate adaptor 50. FIG. 7 and FIG. 8 will be described later.

As specifically shown in FIG. 3 and FIG. 4, a plurality of detents 21*d* projecting inward by a predetermined amount are formed on the inner side at the other end of the coupling wall 21, where the container coupling 20 is fitted to the first supply/discharge cylinder cap 14 and the second supply/discharge cylinder cap 14 to be securely coupled thereto when each detent 21*d* engages with a projection 14*p* at the other end of the supply/discharge cylinder cap 14.

The first supply/discharge port 16 and the second supply/discharge port 16 are respectively positioned on one end side of the first container 10A and the second container 10B and are thereby securely coupled with the container coupling 20, so that the first container 10A and the second container 10B can be securely integrally assembled.

As shown in FIG. 1 and FIG. 2, the side wall of each container 10A, 10B preferably includes a step region 10*s* having a predetermined width and a predetermined depth from substantially the intermediate position in the longitudinal direction to the bottom surface 19, where a shrinkage film 5 may be applied to the step region 10*s* to integrally couple the side surfaces of the containers.

The containers 10A, 10B can be more securely coupled by applying the shrinkage film 5 to the step region 10*s* and integrally coupling the side surfaces of the containers 10A, 10B in addition to coupling the first and the second supply/discharge ports 16, 16 on one end side of the first and the second containers 10A, 10B with the container coupling 20.

The container coupling 20 is also more preferably made of synthetic resin, and configures one type of rigid body. Therefore, the strength and rigidity corresponding to the structure and the mechanical characteristics of the container coupling 20 can be given to the coupling structure of the first container 10A and the second container 10B. In other words, a coupling structure having a significantly high rigidity can be realized compared to the case of simply integrally wrapping and coupling the side walls of the containers 10A, 10B with the shrinkage film 5.

Figure 9:
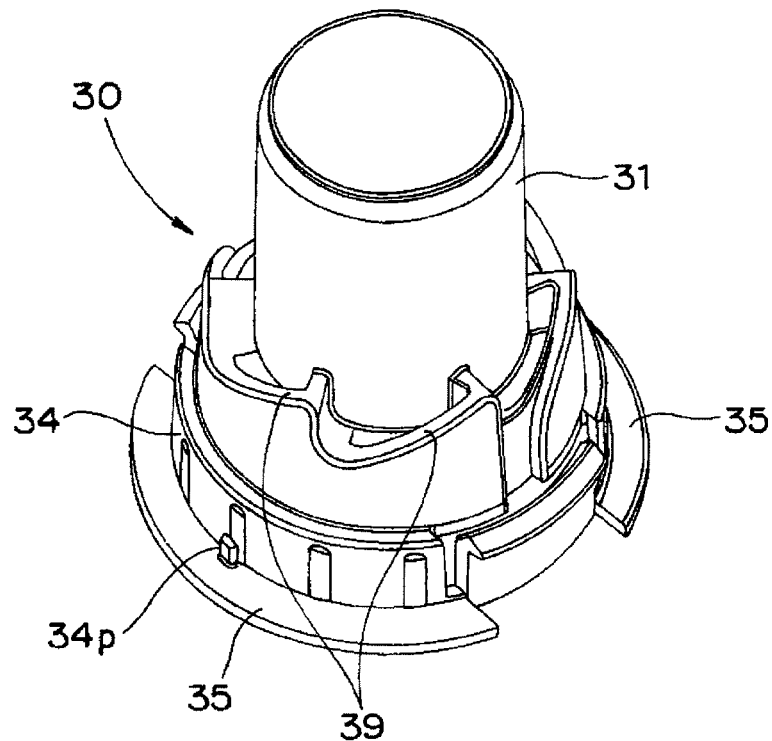
FIG. 9 is an overall perspective view of a nozzle member.
Figure 10:
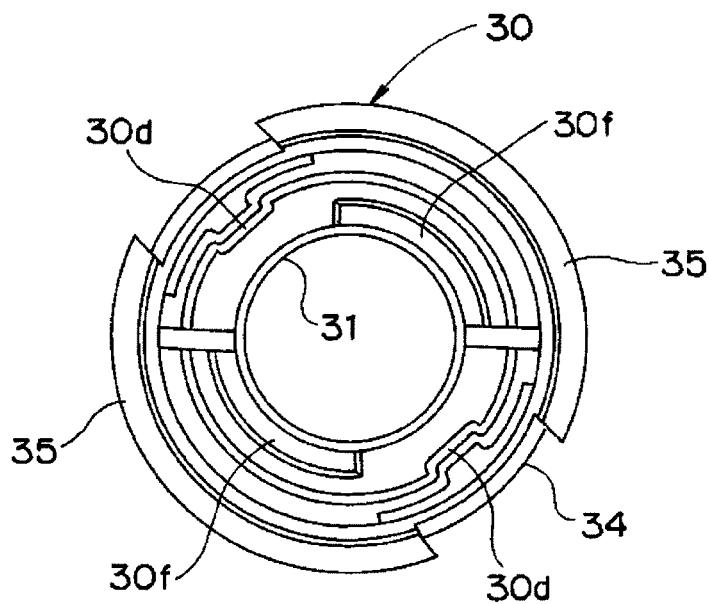
FIG. 10 is an illustrative drawing which shows the nozzle member as seen from the base portion thereof.

FIG. 9 is an overall perspective view of the nozzle member 30, and FIG. 10 is an illustrative drawing which shows the nozzle member 30 as seen from a base portion 34 (nozzle base portion) thereof. As shown in these drawings, the nozzle member 30 has a cylindrical nozzle tube 31 that can be removably fixed to the injection site (not illustrated) of the fluid usage equipment on one end side, where the base portion 34 (nozzle base portion) of the nozzle tube 31 is held rotatably at one end side of the connection cap 40, to be described later, around the longitudinal axis of the nozzle tube 31. The outer periphery of the nozzle tube 31 includes a plurality of (e.g., six in the present embodiment) inclined engagement portions 39 equally arranged at the circumference to engage with an engagement element (not illustrated) of the injection site of the fluid usage equipment at a site connecting to the nozzle base portion 34.

The nozzle tube 31 is configured to be fixed to the injection site of the fluid usage equipment by having a pin-shaped engagement element (not shown) arranged at the injection site of the fluid usage equipment engage with one of the inclined engagement portions 39. Therefore, in the case of the present embodiment, when the nozzle tube 31 is inserted into the injection site of the fluid usage equipment, and the nozzle member 30 is rotated at least about 60 degrees with respect to the connection cap 40, to be described later, in such an inserted state, any one of the six inclined engagement portions 39 can engage with the pin-shaped engagement element arranged at the injection site of the fluid usage equipment, and the nozzle tube 31 can be reliably fixed to the injection site of the fluid usage equipment. The nozzle member 30 is also more preferably made of synthetic resin.

The inclined engagement portion 39 is formed in such a manner that the nozzle member 30 can be rotated in one direction after the nozzle member 30 is fixed with respect to the pin-shaped engagement element (not shown) arranged at the injection site of the fluid usage equipment.

Figure 11:
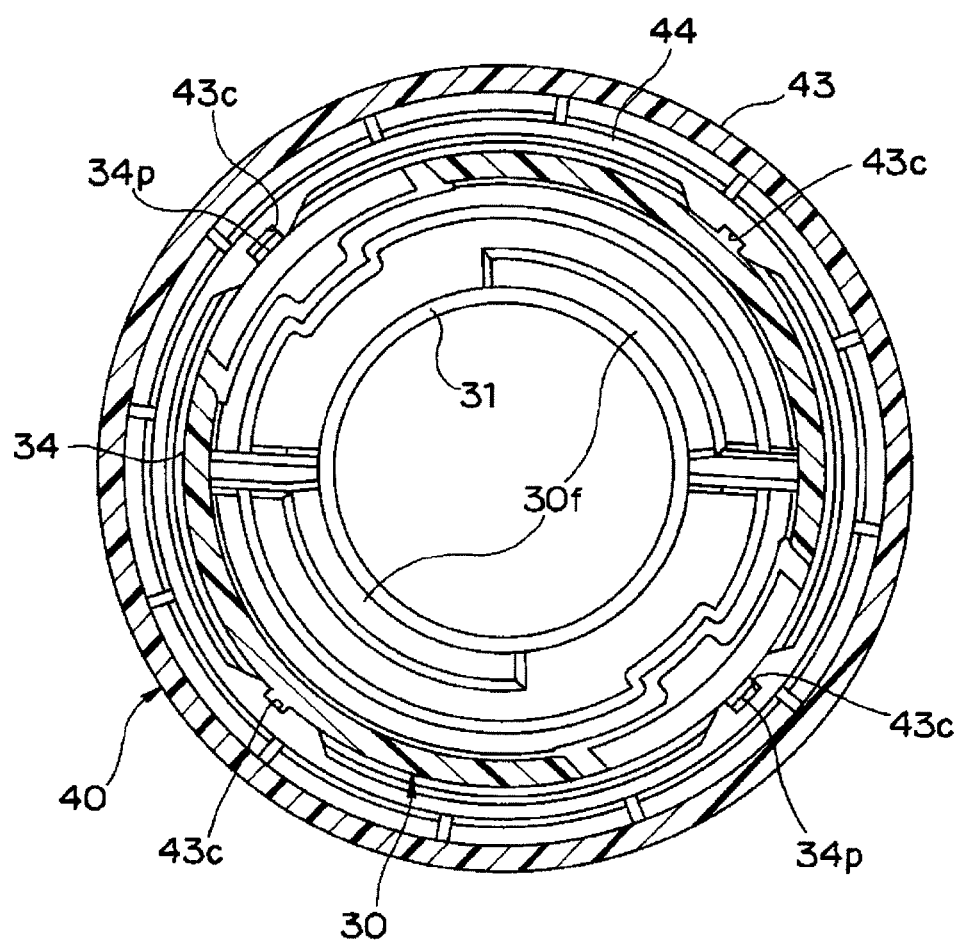
FIG. 11 is an illustrative drawing which shows a critical portion of a cross-sectional view of the nozzle member and a connection cap taken along a line Y11-Y11 in FIG. 3.

As shown in FIG. 1 to FIG. 4, the connection cap 40 has one end rotatably holding (e.g., hold by fitting) the nozzle base portion 34 of the nozzle member 30, and has the other end side fitted to the outer peripheral side of the outer peripheral wall 25 of the container coupling 20 to cover one side of the container coupling 20, and is also preferably made of synthetic resin. FIG. 11 is an illustrative drawing which shows a critical portion of a cross-sectional view of the nozzle member 30 and the connection cap 40 taken along a line Y11-Y11 in FIG. 3. FIG. 11 will be described later.

The connection cap 40 includes a cap main body 41, an end of which fits to the outer peripheral side of the outer peripheral wall 25 of the container coupling 20 to cover one side of the container coupling 20 and define a cap space, a nozzle holder portion 43, formed at the central part of one side of the cap main body 41, for holding the nozzle base portion 34 of the nozzle member 30, and a pair of container side wall locking parts 47 (see FIG. 1). Each of the locking parts 47 bulges out from the end of the cap main body 41 to the other side, for locking each side wall on one side of the first container 10A and the second container 10B.

A plurality of transverse grooves 41*g* (see FIG. 1) having a predetermined width and a predetermined length is formed at a predetermined area in the side wall of the cap main body 41. Locking projections 25*p* are arranged at the sites corresponding to the transverse grooves 41*g* on the outer peripheral side of the outer peripheral wall 25 of the container coupling 20, so that the connection cap 40 is securely held by the container coupling 20 by fitting the locking projections 25*p* into the transverse grooves 41*g*. As shown in FIG. 8, the locking projections 25*p* are integrally formed at a relatively distal end side of a base plate 25*b* (projection base) having flexibility.

As shown in FIG. 5, two locking ribs 48, which form a set, project inward by a predetermined amount and are arranged on the inner surface of the container side wall locking part 47 so as to form a pair for the first container 10A and for the second container 10B. Fitting grooves 10*g* (locked portion), which dimensions are set in correspondence with the length and the projecting height of the respective locking ribs 48, are formed in the side walls on one side of the first container 10A and the second container 10B, respectively.

The locking ribs 48 of each container side wall locking part 47 can be fitted into the fitting grooves 10*g* in the side wall of the first container 10A and the second container 10B with the other end side of the cap main body 41 fitted to the outer periphery of the outer peripheral wall 25 of the container coupling 20 so that the connection cap 40 is fixed to the container coupling 20.

Thus, each side wall of the first and the second containers 10A, 10B is locked to the container side wall locking parts 47 of the connection cap 40 by fitting the locking ribs 48 of the container side wall locking parts 47 into the fitting grooves 10g in the side walls of the first and the second containers 10A, 10B. Therefore, not only the first and the second supply/discharge ports 16 at one end of the first and the second containers 10A, 10B are coupled by the container coupling 20, but also the side wall of each container 10A, 10B is locked to the other side of the connection cap 40, and thereby the first container 10A and the second container 10B are more securely integrated, and for example, twist deformation and the like of the entire unit 1 can also be effectively suppressed even when carrying out the task of removably fixing the nozzle tube 31 to the injection site of the fluid usage equipment.

The intermediate adaptor 50 is held so as to be movable in a direction along the longitudinal axis of the nozzle tube 31 between the container coupling 20 and the nozzle member 30 in the cap space of the connection cap 40, and is also preferably made of synthetic resin.

Figure 12:
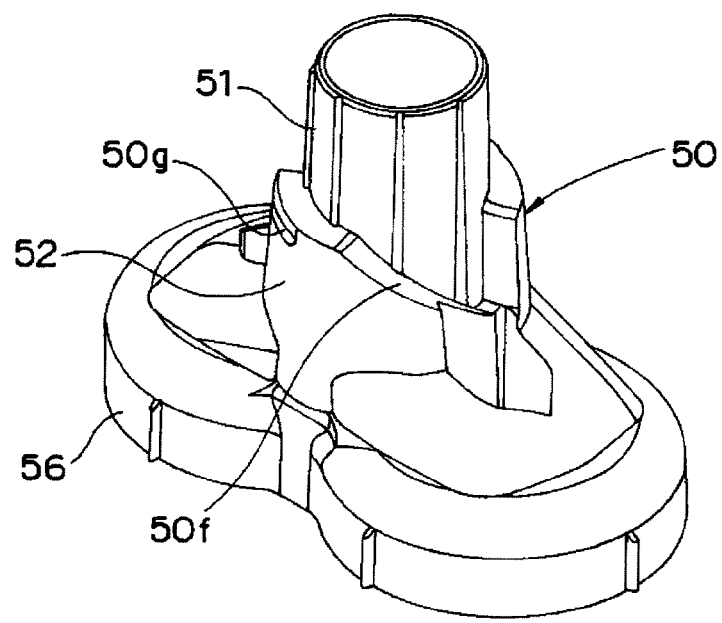
FIG. 12 is an overall perspective view of the intermediate adaptor.
Figure 13:
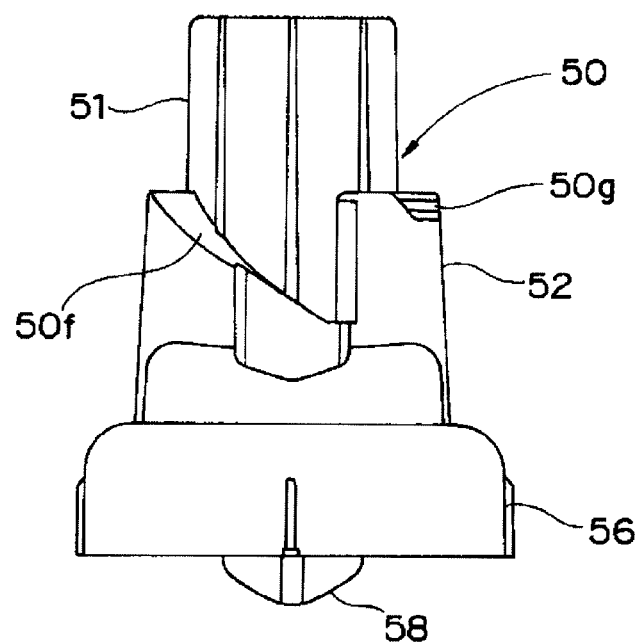
FIG. 13 is a side view of the intermediate adaptor.
Figure 14:
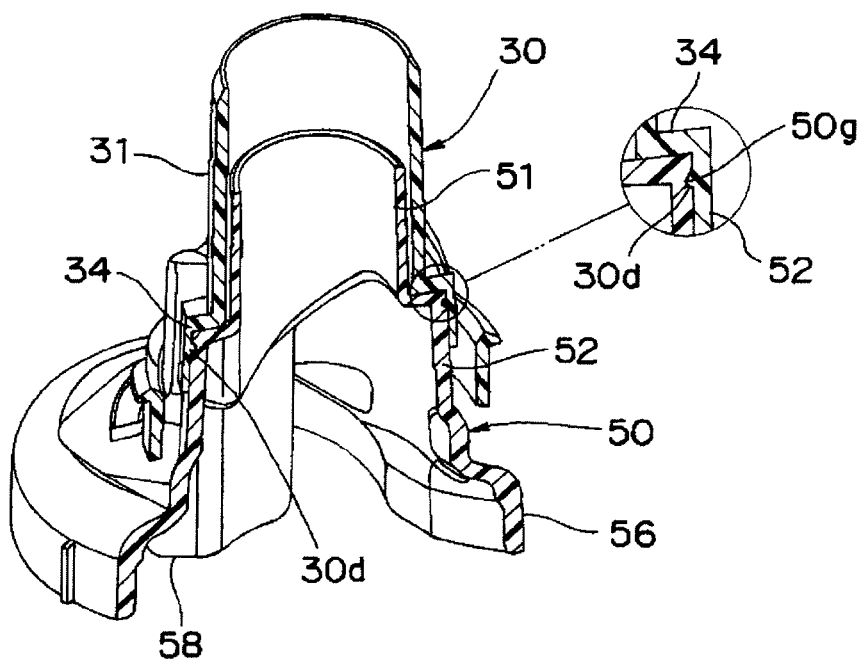
FIG. 14 is a perspective partially broken up view of the intermediate adaptor and the nozzle member illustrating a combined state thereof.
Figure 15:
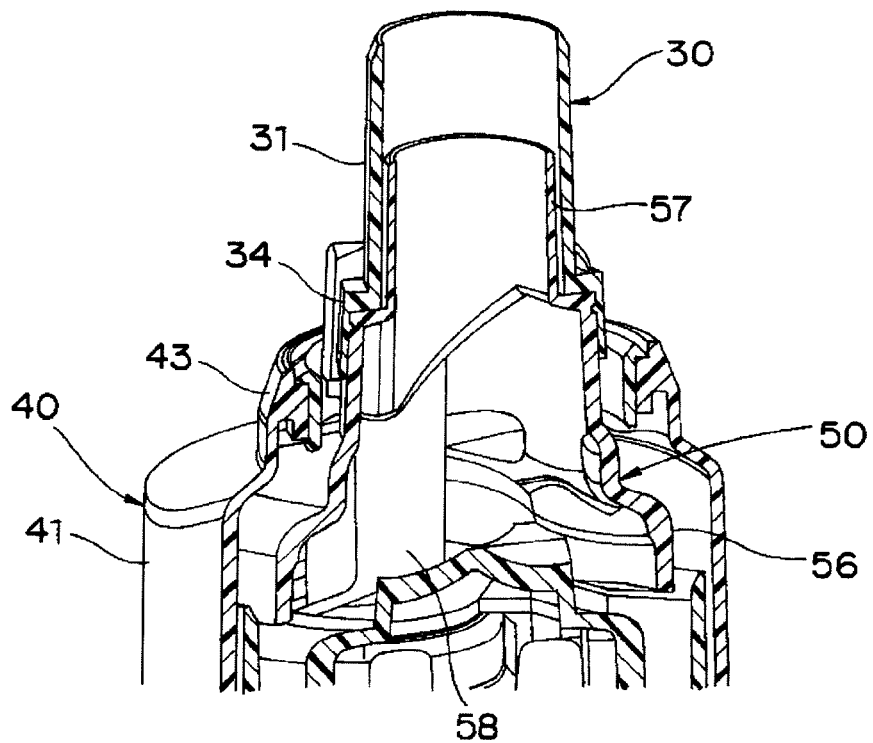
FIG. 15 is a perspective partially broken up view of the intermediate adaptor, the nozzle member and the connection cap illustrating an assembled state thereof.

FIG. 12 is an overall perspective view of the intermediate adaptor 50, FIG. 13 is a side view of the intermediate adaptor 50, FIG. 14 is a perspective partially broken up view of the intermediate adaptor 50 and the nozzle member 30 illustrating a combined state thereof, and FIG. 15 is a perspective partially broken up view of the intermediate adaptor 50, the nozzle member 30, and the connection cap 40 illustrating an assembled state thereof.

As shown in the figures, the intermediate adaptor 50 includes an adaptor tube 51 having a cylindrical shape to be inserted into the nozzle tube 31 of the nozzle member 30, a pair of pusher elements 58 projecting out to the other side from a base portion 52 of the adaptor tube 51, and an adaptor wall 56 having one end side connected to the base portion 52 of the adaptor tube 51 and spreading to the other side so as to surround the pair of pusher elements 58. The other end side of the adaptor wall 56 is positioned so as to correspond to an area between the coupling wall 21 and the outer peripheral wall 25 of the container coupling 20, and faces the flat portion 27.

The pair of pusher elements 58 are positioned and set so as to face the first supply/discharge port 16 of the first container 10A and the second supply/discharge port 16 of the second container 10B, respectively, while being attached in the connection cap 40 of the intermediate adaptor 50. When the intermediate adaptor 50 moves a predetermined amount or more toward the container coupling 20 in the connection cap 40, the pair of pusher elements 58 push-open the closing seal piece 18 of the first supply/discharge port 16 and the closing seal piece 18 of the second supply/discharge port 16 to simultaneously open each supply/discharge port 16 (see FIG. 4).

In the opened state, the end face of the adaptor wall 56 is abutted with the flat portion 27 of the container coupling 20, so that the fluid discharged from the first and the second supply/discharge ports 16 is effectively suppressed from leaking outside the adaptor wall 56.

In other words, the fluids in the first and the second containers 10A, 10B, simultaneously discharged from the first and the second supply/discharge ports 16, are discharged through the nozzle tube 31 of the nozzle member 30 by way of the internal space of the adaptor wall 56 and the adaptor tube 51, and both liquids are mixed in the process of discharge. Therefore, each fluid respectively stored in the two containers 10A, 10B can be discharged from a single nozzle in the mixed state.

The fixing workability is more satisfactory and the injection site of the fluid usage equipment can also be made more compact compared to the case in which two injection ports are handled, since only a single nozzle is arranged on one side (injection side) of the fluid container unit 1.

As the fluids respectively stored in the two containers 10A, 10B are mixed inside the intermediate adaptor 50 and injected at the injection site of the fluid usage equipment in the mixed state, the mixed state of both liquids at the time of use can be more satisfactorily maintained.

In order to hold the end face of the adaptor wall 56 in an abutting state against the flat portion 27 of the container coupling 20 more reliably and stably with the first and the second supply/discharge ports 16 opened, at least one of the coupling wall 21 and the outer peripheral wall 25 of the container coupling 20 as well as the other end side of the adaptor wall 56 is preferably provided with an adaptor wall hold mechanism for keeping the end face of the adaptor wall 56 in the abutting state against the flat portion 27 of the container coupling 20 by locking the other end side of the adaptor wall 56 to at least one of the coupling wall 21 and the outer peripheral wall 25.

As shown in FIG. 7, in the present embodiment, the end face of the adaptor wall 56 is kept in the abutting state against the flat portion 27 of the container coupling 20 more reliably and stably with the first and the second supply/discharge ports 16 open, by combining a pair of outward ribs 21r arranged on the outer periphery of the coupling wall 21 of the container coupling 20 and one inward rib 25r arranged on the inner periphery of the outer peripheral wall 25, and sandwiching the other end side of the adaptor wall 56 between the pair of outward ribs 21r and the inward rib 25r.

The fluid container unit 1 in accordance with the present embodiment includes a supply/discharge port opening mechanism for moving the intermediate adaptor 50 towards the container coupling 20, and opening the first supply/discharge port 16 of the first container 10A and the second supply/discharge port 16 of the second container 10B with the pair of pusher elements 58.

More specifically, the nozzle base portion 34 of the nozzle member 30 is held rotatably around the longitudinal axis of the nozzle tube 31 at one end side of the connection cap 40, where the nozzle tube 31 is configured to be removably fixed to the injection site of the fluid usage equipment (sterilizing agent tank of the apparatus for cleaning the endoscope) by rotating (e.g., greater than or equal to 60 degrees) the nozzle member 30 with respect to the connection cap 40.

As shown in FIG. 10, the supply/discharge port opening mechanism includes a plurality of first inclined surface parts 30f arranged on the inner surface side of the nozzle member 30 (specifically, along the inner periphery of the base of the nozzle tube 31) and inclined along the rotational direction of the nozzle member 30, and a plurality of second inclined surface parts 50f arranged on the outer surface side of the intermediate adaptor 50 (specifically, along the outer periphery of the base portion 52 of the adaptor tube 51) and associated with the first inclined surface parts 30f, as shown in FIG. 11 and FIG. 12.

In the present embodiment, the first inclined surface part 30f is arranged in pairs over approximately 90 degrees at positions facing each other at 180 degrees of the inner periphery of the base of the nozzle tube 31. In correspondence thereto, the second inclined surface part 50f is also arranged in pairs over approximately 90 degrees at positions facing each other at 180 degrees of the outer periphery of the base portion 52 of the adaptor tube 51.

When the nozzle member 30 is rotated by a required angle (e.g., approximately 90 degrees) in one direction, the first inclined surface part 30f rotates by a required angle (e.g., approximately 90 degrees) in one direction, and the second inclined surface part 50f is pushed and moved towards the opposite-nozzle member 30 side so as to be relatively guided along the inclination of the first inclined surface part 30f, and the intermediate adaptor 50 is moved by a predetermined amount towards the container coupling 20 (towards the other side). The pair of pusher elements 58 opens the first and the second supply/discharge ports 16 with the movement of the intermediate adaptor 50.

In other words, in the fluid container unit 1 in accordance with the present embodiment, the nozzle tube 31 is configured to be removably fixed to the injection site of the fluid usage equipment by rotating the nozzle member 30 with respect to the connection cap 40, and the intermediate adaptor 50 is reliably moved towards the container coupling 20 by a predetermined amount through the first inclined surface part 30f and the second inclined surface part 50f by simply rotating the nozzle member 30 by a required angle (e.g., approximately 90 degrees) in one direction. With the movement of the intermediate adaptor 50 towards the container coupling 20 by a predetermined amount, the pair of pusher elements 58 arranged on the other side of the intermediate adaptor 50 is set so as to reliably open the first and the second supply/discharge ports 16.

With the arrangement of such supply/discharge port opening mechanism, the first and the second supply/discharge ports 16 are opened by the pair of pusher elements 58 arranged in the intermediate adaptor 50, and the fluids inside the first and the second containers 10A, 10B can be simultaneously discharged and injected at the injection site of the fluid usage equipment in the mixed state. That is, the nozzle tube 31 can be removably fixed to the injection site of the fluid usage equipment by inserting the nozzle tube 31 to the injection site of the fluid usage equipment, fixing it to, e.g., the pin-shaped engagement element arranged at the injection site, and rotating the nozzle member 30 in one direction in such state, where the first and the second supply/discharge ports 16 are opened by the pair of pusher elements 58 arranged in the intermediate adaptor 50 with the fixing operation. In other words, the fluids inside the first and the second containers 10A, 10B can be simultaneously discharged and injected at the injection site of the fluid usage equipment in a mixed state with a one touch operation with the operation of fixing the nozzle tube 31 to the injection site of the fluid usage equipment.

In the fluid container unit 1 in accordance with the present embodiment, as explained above, the nozzle base portion 34 of the nozzle member 30 is fitted and held rotatably at one end of the connection cap 40. Also, a click sense providing mechanism is arranged at the fitting portion of the nozzle base portion 34 of the nozzle member 30 and the connection cap 40. The click sense providing mechanism is to provide a click sense to the rotating operation of the nozzle member 30 in accordance with the required rotation angle (approximately 90 degrees) of the nozzle member 30 that is enough to let the intermediate adaptor 50 move toward the container coupling 20 by a predetermined amount. The required rotation angle (approximately 90 degrees) of the nozzle member 30 is set to be larger than the rotation angle (approximately 60 degrees) of the nozzle member 30 that is enough to put the nozzle tube 31 in the fixed state at the injection site of the fluid usage equipment, by a predetermined angle (approximately 30 degrees).

The click sense providing mechanism includes, as shown in FIG. 9 more specifically, a small projection 34p arranged at the outer periphery of the nozzle base portion 34 of the nozzle member 30, and an engagement recess 43c formed at the nozzle holder portion 43 of the connection cap 40 to engage the small projection 34p, as shown in FIG. 11.

Two small projections 34p are equally arranged around the circumference at the root of the end brim 35 of the nozzle base portion 34 of the nozzle member 30. As shown in FIG. 11, four engagement recesses 43c are equally arranged at four locations around the circumference at the guide wall of the nozzle holder portion 43 of the connection cap 40. Each engagement recess 43c has a tapered portion on both sides in the rotational direction of the nozzle member 30.

In the unused state (initial state) of the fluid container unit 1, the small projection 34p engages with the engagement recess 43c in the fitted state. When fixing the nozzle tube 31 to the injection site of the fluid usage equipment to inject fluid, the nozzle member 30 is rotated by applying constant or greater rotational torque so that the small projection 34p rides over the groove wall of the engagement recess 43c and disengages from the engagement recess 43c, and thereafter, it is smoothly rotated at low torque while being guided by the guide wall 44 of the nozzle holder portion 43. If the nozzle member 30 is further rotated approximately 90 degrees from the initial state, the small projection 34p again fits into and engages with the engagement recess 43c. To release the engaged state, constant or greater rotational torque needs to be applied again to the nozzle member 30.

Therefore, there is a significant difference between the rotational torque required for the small projection 34p to disengage from the engagement recess 43c and the engagement state to be released, and the rotational torque required when the small projection 34p, which is in the disengaged state, is rotated while being guided by the guide wall 44, and the operator can clearly detect such difference due to the click sense (click feeling) during the rotating operation. With the provision of such click sense, the operator can detect that the nozzle member 30 has been rotated approximately 90 degrees from the initial state, and can finish the operation without continuing the excessive rotating operation.

With the arrangement of the click sense providing mechanism, the operator can detect by the click sense at the time of the rotating operation that the intermediate adaptor 50 has moved towards the container coupling 20 by a predetermined amount and the pair of pusher elements 58 has opened the first supply/discharge port 16 and the second supply/discharge port 16 during the rotating operation of the nozzle member 30 when fixing the nozzle tube 31 to the injection site of the fluid usage equipment to inject fluid. Therefore, the nozzle member 30 can be reliably prevented from being applied with an excessive rotating operation.

The required rotation angle (approximately 90 degrees) of the nozzle member 30 to which the click sense is provided is greater than the rotation angle (approximately 60 degrees) of the nozzle member 30 that is enough to put the nozzle tube 31 in the fixed state to the injection site of the fluid usage equipment, by a predetermined angle (approximately 30 degrees), and thus the nozzle tube 31 can be reliably fixed to the injection site of the fluid usage equipment at the time point when the click sense is detected. Furthermore, as explained above, since an excessive rotating operation will not be applied to the nozzle member 30, excessive torque can be reliably prevented from being applied on the nozzle changing portion of the injection site of the fluid usage equipment.

Moreover, the fluid container unit 1 in accordance with the present embodiment further includes an adaptor holding mechanism for holding the intermediate adaptor 50 in a position where the pair of pusher elements 58 are kept away from the first supply/discharge port 16 and the second supply/discharge port 16 in the unfixed state in which the nozzle tube 31 is not fixed to the injection site of the fluid usage equipment, so that the pusher elements 58, 58 are reliably prevented from unexpectedly opening the first supply/discharge port 16 and the second supply/discharge port 16 in the unfixed state.

More specifically, the adaptor holding mechanism includes a plurality of detents 30d (adaptor retaining detents) arranged on the inner surface side of the nozzle member 30, as shown in FIG. 10, and a plurality of grooves 50g (retained grooves) arranged on the outer surface side of the intermediate adaptor 50 and associated with the adaptor retaining detent 30d, as shown in FIG. 12 and FIG. 13.

In the present embodiment, the adaptor retaining detent 30d is arranged in pairs at positions facing each other at 180 degrees at the inner periphery of the base of the nozzle tube 31. In correspondence thereto, the retained groove 50g is also arranged in pairs at positions facing each other at 180 degrees at the outer periphery of the base portion 52 of the adaptor tube 51.

As shown in FIG. 14 and FIG. 15, the intermediate adaptor 50 is held at the position where the pair of pusher elements 58 are kept away from the first supply/discharge port 16 and the second supply/discharge port 16 in the adaptor retained state in which the retained groove 50g of intermediate adaptor 50 is retained by the adaptor retaining detent 30d of the nozzle member 30 (see FIG. 2 and FIG. 3).

At the time of fixing the nozzle tube 31 to the injection site of the fluid usage equipment, the nozzle member 30 is rotated in one direction from such adaptor retained state, so that the adaptor retaining detent 30d is rotated in one direction and released from the retained groove 50g of the intermediate adaptor 50, and thereby the adaptor retained state is released and the holding state of the intermediate adaptor 50 is also released. The intermediate adaptor 50 can then move towards the container coupling 20 (see FIG. 4).

Therefore, the pair of pusher elements 58 can be reliably kept away from the first and second supply/discharge ports 16 by maintaining the adaptor retained state by means of the adaptor holding mechanism, and the intermediate adaptor 50 including the pair of pusher elements 58 can be reliably moved towards the container coupling 20 by simply rotating the nozzle member 30 in one direction from the adaptor retained state.

As described above, the first closing seal piece 18 and the second closing seal piece 18 are attached to the first supply/discharge port 16 and the second supply/discharge port 16 of the first container 10A and the second container 10B, respectively, in the unfixed state in which the nozzle tube 31 is not fixed to the injection site of the fluid usage equipment. In the present embodiment, the closing seal piece 18 is preferably made of synthetic resin and is preferably push-opened to be displaced in the oblique direction without being broken to open the port when the pair of pusher elements 58 push-open the closing seal pieces 18 of the first and the second supply/discharge ports 16 to open the port, as shown in FIG. 4. Also, as shown with a chain double-dashed line in FIG. 4, the supply/discharge port 16 is partitioned into two apertures 16A, 16b by the closing seal piece 18 displaced in the oblique direction.

The fluid in the containers 10A, 10B is supplied toward the nozzle member 30 through one of the two apertures 16a, 16b (outer aperture 16b positioned on the outer side), and the air is introduced into the container 10A, 10B through the other aperture (inner aperture 16a positioned on the inner side).

As the push-opened closing seal piece 18 separates the supply/discharge port 16 into two apertures 16a, 16b, and the fluid in the containers 10A, 10B is supplied towards the nozzle member 30 from one aperture 16b whereas the air is introduced into the containers 10A, 10B from the other aperture 16a, the air can be easily introduced into the containers 10A, 10B, and a smooth fluid supply with suppressed pulsation can be carried out.

As described above, according to the present embodiment, in the fluid container unit 1 configured by integrally assembly of the first container 10A and the second container 10B, which respectively store different types of fluid in a parallel arrangement, the first supply/discharge port 16 positioned on one end of the first container 10A and the second supply/discharge port 16 positioned on one end of the second container 10B are coupled with the container coupling 20, thereby the first container 10A and the second container 10B can be securely integrated and assembled.

Further, with the arrangement of the supply/discharge port opening mechanism, the first supply/discharge port 16 and the second supply/discharge port 16 can be opened with the pair of pusher elements 58 arranged in the intermediate adaptor 50. That is, the fluid in the first and the second containers 10A, 10B can be simultaneously discharged and injected into the injection site of the fluid usage equipment with a one touch operation, along with the fixing operation of removably fixing the nozzle tube 31 to the injection site of the fluid usage equipment.

Furthermore, a single nozzle 31 is arranged on one end (injection side) of the fluid container unit 1, and the fluid in the first and the second containers 10A, 10B is injected into the injection site of the fluid usage equipment through the single nozzle 31, and hence the fixing work to the injection site of the fluid usage equipment can be easily and rapidly carried out, and the workability thereof can be greatly enhanced as compared to the case where two injection ports are employed.

Moreover, the fluid in the first container 10A and the second container 10B simultaneously discharged from the first supply/discharge port 16 and the second supply/discharge port 16 is mixed in the process of being discharged through the single nozzle member 30, and is injected into the injection site of the fluid usage equipment in such mixed state, and hence a more satisfactory mixed state can be obtained. Furthermore, the injection site of the fluid usage equipment also merely needs to receive the single nozzle 31 since the single nozzle 31 is arranged at the injection site of the fluid container unit 1, and thereby the injection site of the fluid usage equipment can be made more compact as compared to when receiving two injection ports.

In the embodiment described above, when the pair of pusher elements 58 push-opens the closing seal pieces 18 to open the first and the second supply/discharge ports 16, the closing seal piece 18 preferably made of synthetic resin is preferably push-opened so as to be displaced in the oblique direction without being broken, but instead, the closing seal piece may be made from a relatively easily breakable material such as aluminum foil, so that the closing seal piece is push-opened by being broken to open the port when the pair of pusher elements 58 push-open each closing seal piece 18 to open the first and the second supply/discharge ports 16. In this case, however, it is difficult to separate the supply/discharge port into two apertures by the push-opened (broken) closing seal piece.

The above embodiment is related to the fluid container unit 1 used to mix and supply a predetermined sterilizing agent to the sterilizing agent tank of the apparatus for cleaning the endoscope. However the present invention is not limited to such case, and can be effectively applied to various other cases in which the fluid container unit is configured by integrally assembling two containers, which store different types of fluid, in parallel arrangement.

Thus, the present invention is not limited to the above embodiments, and it should be recognized that various modifications and improvements can be made within a scope not deviating from the gist of the invention.

The fluid container unit of the present invention relates to the fluid container unit configured by integrally assembling two containers, which store different types of fluid, in parallel arrangement, where the fixing workability to the injection site of the fluid usage equipment is easier, and the injection site can be made more compact. Also, it can be effectively utilized, for example, in the fluid container unit and the like used to mix and supply a predetermined sterilizing agent to the sterilizing agent tank of the apparatus for cleaning the endoscope.

The invention claimed is:

1. A fluid container unit configured by integrally-assembling a first container and a second container for respectively accumulating different kinds of fluids in a parallel arrangement, the fluid container unit comprising:
   a container coupling for coupling a first supply/discharge port located at one end of the first container with a second supply/discharge port located at one end of the second container;
   a single nozzle member having a nozzle tube;
   a connection cap having a first end for holding a base portion of the nozzle member and a second end for covering one side of the container coupling by fitting around an outer periphery thereof;
   an intermediate adaptor having a pair of pusher elements facing the first supply/discharge port and the second supply/discharge port respectively, the intermediate adaptor being held movably in a direction along a longitudinal axis of the nozzle tube in the connection cap; and
   a supply/discharge port opening mechanism for moving the intermediate adaptor toward the container coupling and opening the first supply/discharge port and the second supply/discharge port by the pair of pusher elements,
   wherein the base portion of the nozzle member is held rotatably around the longitudinal axis of the nozzle tube at the first end of the connection cap;
   wherein the nozzle member is configured so as to be capable of being removably fixed to an injection site of fluid usage equipment;
   wherein the supply/discharge port opening mechanism comprises a first inclined surface part which is provided on an inner surface of the nozzle member and is inclined along a rotational direction of the nozzle member, and a second inclined surface part which is provided on an outer surface of the intermediate adaptor so as to be associated with the first inclined surface part; and
   wherein rotating the nozzle member by a required angle in one direction causes the first inclined surface part to rotate by a required angle in one direction and to push the second inclined surface part in a direction that is opposite the nozzle member side, thereby moving the intermediate adaptor forward toward the container coupling by a predetermined amount and opening the first supply/discharge port and the second supply/discharge port by the pair of pusher elements.

2. A fluid container unit according to claim 1,
   wherein by inserting the nozzle tube of the nozzle member into the injection site of the fluid usage equipment, thereafter rotating the nozzle member by a required angle in the one direction while maintaining the insertion state, the nozzle tube can be removably fixed to the injection site of the fluid usage equipment, and the intermediate adaptor is moved toward the container coupling by a predetermined amount, and the pair of pusher elements open the first supply/discharge port and the second supply/discharge port.

3. A fluid container unit according to claim 1,
   wherein the base portion of the nozzle member is held by fitting at the one end of the connection cap;
   wherein at a fitting portion between the base portion of the nozzle member and the connection cap, a click sense providing mechanism for providing a click sense to a rotating operation of the nozzle member in accordance with a required rotation angle of the nozzle member which is enough to let the intermediate adaptor to move toward the container coupling by the predetermined amount; and
   wherein the required rotation angle of the nozzle member is set to be larger by a predetermined angle than a rotation angle that is sufficient to put the nozzle tube into a fixed state to the injection site of the fluid usage equipment.

4. A fluid container unit according to claim 1,
   wherein a first closing seal piece and a second closing seal piece are attached at the first and the second supply/discharge ports, respectively, for closing the first and second supply/discharge ports in an unfixed state in which the nozzle tube is not fixed to the injection site of the fluid usage equipment;
   wherein the pair of pusher elements open the first and second supply/discharge ports by pushing open the first and the second closing seal pieces, respectively; and
   wherein each of the first and second supply/discharge ports is separated into two apertures by a push-opened closing seal piece, and thereafter, the fluid in the container is supplied to the nozzle member side through one aperture, while air is introduced into the respective container through the other aperture.

5. A fluid container unit according to claim 1,
   wherein the first container is provided with a first supply/discharge cylinder that projects from an end of the first container, and the first supply/discharge port is formed inside of the first supply/discharge cylinder;
   wherein the second container is provided with a second supply/discharge cylinder that projects from an end of the second container, and the second supply/discharge port is formed inside of the second supply/discharge cylinder;
   wherein the container coupling is provided with a coupling wall for coupling the first supply/discharge cylinder and the second supply/discharge cylinder, an outer peripheral wall surrounding the coupling wall at a predetermined distance therefrom and a flat portion for connecting an end of the outer peripheral wall and an end of the coupling wall;
   wherein the intermediate adaptor is provided with an adaptor wall for surrounding the pair of pusher elements; and
   wherein an end surface of the adaptor wall abuts against the flat portion of the container coupling, in a state in which the pair of pusher elements open the first and the second supply/discharge ports by moving the intermediate adaptor toward the container coupling side.

6. A fluid container unit according to claim 5,
   wherein at least one of the coupling wall, the outer peripheral wall and the adaptor wall are provided with an adaptor wall hold mechanism for keeping the end surface of the adaptor wall in an abutting state against the flat portion of the container coupling, by locking the adaptor wall with at least one of the coupling wall and the outer peripheral wall.

7. A fluid container unit according to claim 1, wherein a side of the connection cap is provided with a container side wall locking part for locking each side wall of the first and the second containers, and each side wall of the first and the second containers is provided with a locked portion for being locked by the container side wall locking part.

8. A fluid container unit configured by integrally-assembling a first container and a second container for respectively accumulating different kinds of fluids in a parallel arrangement, the fluid container unit comprising:
   a container coupling for coupling a first supply/discharge port located at one end of the first container with a second supply/discharge port located at one end of the second container;
   a single nozzle member having a nozzle tube;
   a connection cap having one end for holding a base portion of the nozzle member and another end for covering one side of the container coupling by fitting around an outer periphery thereof;
   an intermediate adaptor having a pair of pusher elements facing the first supply/discharge port and the second supply/discharge port, respectively, the intermediate adaptor being held movably in a direction along a longitudinal axis of the nozzle tube in the connection cap; and
   a supply/discharge port opening mechanism for moving the intermediate adaptor toward the container coupling and opening the first supply/discharge port and the second supply/discharge port by the pair of pusher elements,
   wherein the fluid container unit further comprises an adaptor holding mechanism which holds the intermediate adaptor in a position where the pair of pusher elements are kept away from the first supply/discharge port and the second supply/discharge port, in an unfixed state in which the nozzle tube is not fixed to the injection site of the fluid usage equipment.

9. A fluid container unit according to claim 8,
   wherein the adaptor holding mechanism comprises an adaptor retaining portion provided on an inner surface of the nozzle member, and a retained portion which is provided on an outer surface of the intermediate adaptor and associated with the adaptor retaining portion;
   wherein the intermediate adaptor is held in a position where the pair of pusher elements are kept away from the first supply/discharge port and the second supply/discharge port, in an adaptor retained state in which the retained portion of the intermediate adaptor is retained by the adaptor retaining portion of the nozzle member; and
   wherein by rotating the nozzle member in one direction from the adaptor retained state, the adaptor retaining portion is rotated in the one direction and released from the retained portion, thereby the adaptor retained state is released and also the intermediate adaptor holding state is released, and further thereby the intermediate adaptor is allowed to move toward the container coupling.

10. A method for injecting different kinds of fluids into a predetermined fluid usage equipment, the method comprising:
   a first step of preparing a fluid container unit configured by integrally-assembling a first container and a second container for respectively accumulating the different kinds of fluids in a parallel arrangement, the fluid container unit comprising:
   a) a container coupling for coupling a first supply/discharge port located at one end of the first container with a second supply/discharge port located at one end of the second container;
   b) a single nozzle member having a nozzle tube, and being configured so as to be removably fixed to an injection site of the fluid usage equipment;
   c) a connection cap having a first end for holding a base portion of the nozzle member and a second end for covering one side of the container coupling by fitting around an outer periphery thereof;
   d) an intermediate adaptor having a pair of pusher elements facing the first supply/discharge port and the second supply/discharge port respectively, the intermediate adaptor being held movably in a direction along a longitudinal axis of the nozzle tube in the connection cap; and
   e) a supply/discharge port opening mechanism for moving the intermediate adaptor toward the container coupling and opening the first supply/discharge port and the second supply/discharge port by the pair of pusher elements,
   a second step of inserting the single nozzle member into a single injection port at an injection site of the fluid usage equipment,
   a third step of rotating the nozzle member by a required angle in one direction after said second step,
   wherein the base portion of the nozzle member of the fluid container unit is held rotatably around the longitudinal axis of the nozzle tube at one end of the connection cap;
   wherein the supply/discharge port opening mechanism comprises a first inclined surface part which is provided on an inner surface of the nozzle member and inclines along a rotational direction of the nozzle member, and a second inclined surface part which is provided on an outer surface of the intermediate adaptor so as to be associated with the first inclined surface part; and
   wherein, in said third step, rotating the nozzle member by the required angle in one direction causes the first inclined surface part to rotate by the required angle in one direction and to push the second inclined surface part away from a nozzle member side, and thereby the intermediate adaptor is moved forward the container coupling by a predetermined amount, and the pair of pusher elements open the first supply/discharge port and the second supply/discharge port.

11. A method according to claim 10,
   wherein the base portion of the nozzle member is held by fitting at the first end of the connection cap;
   wherein at a fitting portion between the base portion of the nozzle member and the connection cap, a click sense providing mechanism for providing a click sense to a rotating operation of the nozzle member in accordance with the required rotation angle of the nozzle member which is enough to let the intermediate adaptor move toward the container coupling by a predetermined amount; and
   wherein the required rotation angle of the nozzle member in said third step is set to be larger by a predetermined angle than a rotation angle that is enough to put the nozzle tube into a fixed state at the injection site of the fluid usage equipment.

12. A method according to claim 10,
wherein by inserting the nozzle tube of the nozzle member into the injection site of the fluid usage equipment in said second step, and thereafter rotating the nozzle member by the required angle in the one direction while maintaining the insertion state in said third step, the nozzle tube is removably fixed to the injection site of the fluid usage equipment, and the intermediate adaptor is moved toward the container coupling by the predetermined amount, and the pair of pusher elements open the first supply/discharge port and the second supply/discharge port.

13. A method according to claim 12,
wherein the base portion of the nozzle member is held by fitting at the first end of the connection cap;
wherein at a fitting portion between the base portion of the nozzle member and the connection cap, a click sense providing mechanism for providing a click sense to a rotating operation of the nozzle member in accordance with the required rotation angle of the nozzle member which is enough to let the intermediate adaptor move toward the container coupling by the predetermined amount; and wherein the required rotation angle of the nozzle member in said third step is set to be larger by a predetermined angle than a rotation angle that is enough to put the nozzle tube into a fixed state at the injection site of the fluid usage equipment.

14. A method according to claim 10,
wherein a first closing seal piece and a second closing seal piece are attached at the first supply/discharge port and the second supply/discharge port, respectively, for closing the first and second supply/discharge ports in an unfixed state in which the nozzle tube is not fixed to the injection site of the fluid usage equipment;
wherein, in said third step, the pair of pusher elements open the first and second supply/discharge ports by pushing open the first and second closing seal pieces, respectively; and
wherein each of the supply/discharge ports is separated into two apertures by a push-opened closing seal piece, and thereafter, the fluid in the container is supplied to the nozzle member side through one aperture, while air is introduced into the container through the other aperture.

* * * * *

UNITED STATES PATENT AND TRADEMARK OFFICE
CERTIFICATE OF CORRECTION

| | | |
|---|---|---|
| PATENT NO. | : 8,684,233 B2 | Page 1 of 1 |
| APPLICATION NO. | : 13/124165 | |
| DATED | : April 1, 2014 | |
| INVENTOR(S) | : Nishio et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
Seventeenth Day of November, 2015

Michelle K. Lee
*Director of the United States Patent and Trademark Office*